(12) United States Patent
Gartside et al.

(10) Patent No.: US 8,084,659 B2
(45) Date of Patent: Dec. 27, 2011

(54) HEXENE UPGRADING

(75) Inventors: Robert J. Gartside, Summit, NJ (US); Thulasidas Chellppannair, East Brunswick, NJ (US)

(73) Assignee: Lummus Technology, Inc.

( * ) Notice: Subject to any disclaimer, the term of this patent is extended or adjusted under 35 U.S.C. 154(b) by 279 days.

(21) Appl. No.: 12/603,283

(22) Filed: Oct. 21, 2009

(65) Prior Publication Data
US 2010/0099934 A1    Apr. 22, 2010

Related U.S. Application Data (60) Provisional application No. 61/107,528, filed on Oct. 22, 2008.

(51) Int. Cl.
*C07C 5/25* (2006.01)
*C07C 41/05* (2006.01)
*C07C 41/09* (2006.01)

(52) U.S. Cl. .................. 585/324; 585/664; 568/579

(58) Field of Classification Search ............ 585/324, 585/664; 568/579
See application file for complete search history.

(56) References Cited

U.S. PATENT DOCUMENTS

| | | |
|---|---|---|
| 2,480,940 A | 9/1949 | Leum et al. |
| 2,922,822 A | 1/1960 | Beach |
| 3,489,243 A | 1/1970 | Prescott et al. |
| 4,270,929 A | 6/1981 | Dang Vu et al. |
| 4,302,356 A | 11/1981 | Smith, Jr. |
| 4,330,679 A | 5/1982 | Kohler et al. |
| 4,443,559 A | 4/1984 | Smith, Jr. |
| 4,538,018 A | 8/1985 | Carter |
| 4,751,343 A | 6/1988 | Reinhardt et al. |
| 4,950,632 A | 8/1990 | Drake |
| 5,012,031 A | 4/1991 | Schleppinghoff et al. |
| 5,105,048 A | 4/1992 | Brake |
| 5,105,049 A | 4/1992 | Hasselbring |
| 5,166,114 A | 11/1992 | An-hsiang |
| 5,198,563 A | 3/1993 | Reagen et al. |
| 5,434,327 A * | 7/1995 | Chin et al. ............. 585/533 |
| 5,523,507 A | 6/1996 | Reagen et al. |
| 5,730,843 A | 3/1998 | Groten et al. |
| 5,811,618 A | 9/1998 | Wu |

(Continued)

FOREIGN PATENT DOCUMENTS

EP    1942090 A2    7/2008

(Continued)

OTHER PUBLICATIONS

International Search Report and Written Opinion issued May 20, 2010 in corresponding International Application No. PCT/US2009/061677 (7 pages).

*Primary Examiner* — Thuan Dinh Dang
(74) *Attorney, Agent, or Firm* — Osha • Liang LLP (57) ABSTRACT

Embodiments disclosed herein provide processes for upgrading the hexene stream to valuable end products, including ethers, high purity 1-hexene, and, alternatively, high purity isohexene. Hexene upgrading may be performed in embodiments disclosed herein by first removing isohexene from the admixture. The isohexene may undergo etherification with one or more alcohols, facilitating the separation of the isohexene (in the form of an ether) from the normal hexenes. Second, the normal hexenes may be isomerized to convert internal hexene olefins (2-hexenes and 3-hexenes) to the desired alpha olefin, 1-hexene. The 1-hexene may then be separated from unreacted components to yield a high purity 1-hexene product.

33 Claims, 3 Drawing Sheets

U.S. PATENT DOCUMENTS

| | | |
|---|---|---|
| 5,968,866 A | 10/1999 | Wu |
| 6,455,648 B1 | 9/2002 | Freeman et al. |
| 6,521,806 B1 | 2/2003 | Tamura et al. |
| 6,531,555 B2 | 3/2003 | Whiteker |
| 6,727,396 B2 | 4/2004 | Gartside |
| 6,743,960 B2 | 6/2004 | Wang et al. |
| 6,777,582 B2 | 8/2004 | Gartside et al. |
| 6,927,313 B2 | 8/2005 | Bianchini et al. |
| 7,273,959 B2 | 9/2007 | Drent et al. |
| 7,355,087 B2 | 4/2008 | Cano et al. |
| 7,384,886 B2 | 6/2008 | Knudsen et al. |
| 7,399,895 B2 | 7/2008 | Briggs et al. |
| 7,414,006 B2 | 8/2008 | McConville et al. |
| 7,425,661 B2 | 9/2008 | McConville et al. |
| 2003/0166456 A1 | 9/2003 | Wass |

FOREIGN PATENT DOCUMENTS

| | | |
|---|---|---|
| JP | 10045638 A | 2/1998 |

* cited by examiner

HEXENE UPGRADING

CROSS-REFERENCE TO RELATED APPLICATION

This application, pursuant to 35 U.S.C. §119(e), claims priority to U.S. Provisional Application Ser. No. 61/107,528, filed Oct. 22, 2008, which is incorporated herein by reference in its entirety.

BACKGROUND OF DISCLOSURE

1. Field of the Disclosure

Embodiments disclosed herein relate to the production of linear alpha olefins. More particularly, embodiments disclosed herein relate to the production of linear alpha olefins, such as hexene-1, from a mixture of internal- and iso-olefins, such as isohexene, 2-hexene, and 3-hexene.

2. Background

There is a growing need for terminal (alpha) olefins such as 1-hexene. 1-hexene may be produced by the selective oligomerization of ethylene, for example. In general, the oligomerization is conducted in the presence of a homogeneous catalyst, such as an alkylated metal catalyst. Long residence times are used to produce hydrocarbon chains of varying lengths. Ethylene oligomerization produces a wide spectrum of linear alpha olefin products, including 1 butene, 1 hexene, 1 octene etc. In addition, depending upon the catalyst used, there are internal olefins such as 2-hexene, 3-hexene, and iso-hexene.

Alpha olefins may also be produced by the isolation of the alpha olefin from a hydrocarbon stream containing a relatively high concentration of the 1-isomer. However, such streams often contain numerous components having a similar or close boiling point to that of the desired 1-isomer.

Alpha olefins, specifically 1-butene and 1-hexene, can be produced from C4 streams utilizing metathesis in combination with double bond isomerization. U.S. Pat. No. 6,727,396 describes such a process and is incorporated herein by reference. A critical step in that process is the removal of isobutylene prior to the metathesis step to avoid the production of isohexenes that would represent a contaminant in a 1-hexene stream to be used as a comonomer in polymerization processes.

Regardless of the source of mixed hexenes, production of comonomer grade 1-hexene requires the removal of the isohexenes and the separation of the internal hexenes. Extensive fractionation is required to separate the alpha olefins having different internal or iso-olefins. Further, given the very low relative volatility between certain of these isomers, fractionation is impractical. Accordingly, there exists a need for processes for the efficient production and recovery of 1-hexene from mixed hexene streams.

SUMMARY OF THE DISCLOSURE

In one aspect, embodiments disclosed herein relate to a process for upgrading a mixed hexene stream, the process comprising: feeding an alcohol and a mixed hydrocarbon stream comprising isohexene, 2-hexene, and 3-hexene to an etherification reaction zone containing an etherification catalyst; contacting the isohexene and the alcohol in the presence of the etherification catalyst at reaction conditions of temperature and pressure to convert at least a portion of the isohexene and the alcohol to an ether; recovering an effluent from the etherification reactor comprising ether, 2-hexene, 3-hexene, and unreacted alcohol and isohexene; separating the etherification reactor effluent in a first distillation system to recover a bottoms fraction comprising the ether and an overheads fraction comprising the 2-hexene, 3-hexene, and the unreacted alcohol and isohexene; feeding the overheads fraction to an isomerization reaction zone containing an isomerization catalyst; contacting the 2-hexene and 3-hexene with the isomerization catalyst at conditions of temperature and pressure to convert at least a portion of the 2-hexene and the 3-hexene to 1-hexene; recovering an effluent from the isomerization reaction zone comprising 2-hexene, 3-hexene, isohexene, and 1-hexene; separating the isomerization effluent in a second distillation system to recover a bottoms fraction comprising 2-hexene and 3-hexene and an overheads fraction comprising 1-hexene.

In another aspect, embodiments disclosed herein relate to a process for upgrading a mixed hexene stream, the process comprising: feeding an alcohol and mixed hydrocarbon stream comprising isohexene, 2-hexene, and 3-hexene to an etherification reaction zone containing an etherification catalyst; contacting the isohexene and the alcohol in the presence of the etherification catalyst at reaction conditions of temperature and pressure to convert at least a portion of the isohexene and the alcohol to an ether; recovering an effluent from the etherification reactor comprising ether, 2-hexene, 3-hexene, and unreacted alcohol and isohexene; separating the etherification reactor effluent in a first distillation system to recover a bottoms fraction comprising the ether and an overheads fraction comprising the 2-hexene, 3-hexene, and the unreacted alcohol and isohexene; feeding a portion of the overheads fraction comprising unreacted alcohol and 1-hexene to a fixed bed reactor system containing a second etherification catalyst, which may be the same or different than the etherification catalyst; contacting the isohexene and the alcohol in the presence of the second etherification catalyst at conditions of temperature and pressure to convert at least a portion of the isohexene and the alcohol to an ether; recovering an effluent from the fixed bed reactor system comprising ether, 2-hexene, 3-hexene, and any unreacted alcohol and isohexene; feeding the effluent from the fixed bed reactor system to the separating the etherification reactor effluent; feeding a portion of the overheads fraction to an isomerization reaction zone containing an isomerization catalyst; contacting the 2-hexene and 3-hexene in the overheads fraction with the isomerization catalyst at conditions of temperature and pressure to convert at least a portion of the 2-hexene and the 3-hexene to 1-hexene; recovering an effluent from the isomerization reaction zone comprising 2-hexene, 3-hexene, isohexene, and 1-hexene; separating the isomerization effluent in a second distillation system to recover a bottoms fraction comprising 2-hexene and 3-hexene and an overheads fraction comprising 1-hexene.

In another aspect, embodiments disclosed herein relate to a process for upgrading a mixed hexene stream, the process comprising: feeding an alcohol and a mixed hydrocarbon stream comprising isohexene, 2-hexene, and 3-hexene to an etherification reaction zone containing an etherification catalyst; contacting the isohexene and the alcohol in the presence of the etherification catalyst at reaction conditions of temperature and pressure to convert at least a portion of the isohexene and the alcohol to an ether; recovering an effluent from the etherification reaction zone comprising ether, 2-hexene, 3-hexene, and unreacted alcohol and isohexene; feeding the effluent from the etherification reaction zone to a catalytic distillation reactor system containing a second etherification catalyst, which may be the same or different than the etherification catalyst; concurrently in the catalytic distillation reactor system: contacting the isohexene and the alcohol in the presence of the second etherification catalyst at conditions of temperature and pressure to convert at least a portion of the isohexene and the alcohol to additional ether; separating the etherification reactor effluent and the additional ether to recover a bottoms fraction comprising the ether and an overheads fraction comprising the 2-hexene, 3-hexene, and any unreacted alcohol and isohexene; feeding at least a portion of the overheads fraction to an isomerization reaction zone containing an isomerization catalyst; contacting the 2-hexene and 3-hexene in the overheads fraction with the isomerization catalyst at conditions of temperature and pressure to convert at least a portion of the 2-hexene and the 3-hexene to 1-hexene; recovering an effluent from the isomerization reaction zone comprising 2-hexene, 3-hexene, isohexene, and 1-hexene; separating the isomerization effluent in a second distillation system to recover a bottoms fraction comprising 2-hexene and 3-hexene and an overheads fraction comprising 1-hexene.

Other aspects and advantages will be apparent from the following description and the appended claims.

DETAILED DESCRIPTION

In one aspect, embodiments herein relate to the production of linear alpha olefins. More particularly, embodiments disclosed herein relate to the production of linear alpha olefins, such as hexene-1, from a mixture of internal- and iso-olefins, such as isohexene, 2-hexene, and 3-hexene.

In some embodiments disclosed herein, reactors used to perform various reactions may include catalytic distillation reactor systems. Within the scope of this application, the expression "catalytic distillation reactor system" denotes an apparatus in which the catalytic reaction and the separation of the products take place at least partially simultaneously. The apparatus may comprise a conventional catalytic distillation column reactor, where the reaction and distillation are concurrently taking place at boiling point conditions, or a distillation column combined with at least one side reactor, where the side reactor may be operated as a liquid phase reactor or a boiling point reactor. While both catalytic distillation reactor systems described may be preferred over conventional liquid phase reaction followed by separations, a catalytic distillation column reactor may have the advantages of decreased piece count, reduced capital cost, increased catalyst productivity per pound of catalyst, efficient heat removal (heat of reaction may be absorbed into the heat of vaporization of the mixture), and a potential for shifting equilibrium. Divided wall distillation columns, where at least one section of the divided wall column contains a catalytic distillation structure, may also be used, and are considered "catalytic distillation reactor systems" herein.

Mixed hexene streams may include 1-hexene, 2-hexenes, 3-hexenes, and isohexene, among other components. Embodiments disclosed herein provide processes for upgrading the hexene stream to valuable end products, including ethers, high purity 1-hexene, and, alternatively, high purity isohexene. Hexene upgrading may be performed in embodiments disclosed herein by first removing isohexene from the admixture. The isohexene may undergo etherification with one or more alcohols, facilitating the separation of the isohexene (in the form of an ether) from the normal hexenes. Second, the normal hexenes may be isomerized to convert internal hexene olefins (2-hexenes and 3-hexenes) to the desired alpha olefin, 1-hexene. The 1-hexene may then be separated from unreacted components to yield a high purity 1-hexene product.

Hydrocarbon feedstocks for use in embodiments of the hexene upgrading processes described herein may include $C_3$ to $C_9$ and higher hydrocarbons. For example, refinery streams are usually separated by fractional distillation. A light naphtha cut is one such refinery stream and because they often contain compounds that are very close in boiling points, the separations are not precise. Thus, a $C_6$ stream, for instance, may include $C_4$s and up to $C_8$s and higher. These components may be saturated (alkanes), unsaturated (mono-olefins), and poly-unsaturated (diolefins, for example). Additionally, the components may be any or all of the various isomers of the individual compounds. Other hydrocarbon streams of $C_4$ to $C_9$ carbon atoms may be used in embodiments disclosed herein.

In some embodiments, hydrocarbon feedstocks may include a $C_6$ cut, which may include $C_4$ to $C_8$ or higher hydrocarbons (i.e., $C_{9+}$), including olefins. In other various embodiments, hydrocarbon feedstocks may include mixtures of one or more of $C_4$, $C_5$, $C_6$, and $C_{7+}$ hydrocarbons, where the mixture includes olefinic compounds and paraffinic compounds. The above described streams may include $C_4$ to $C_7$ streams, gasoline fractions, FCC gasoline, coker gasoline, and other refinery streams having similar properties.

Saturated compounds included in the above described hydrocarbon streams may include various isomers of butane, various isomers of pentane, and various isomers of hexane, among others, for example. Olefinic compounds included in the above described hydrocarbon streams may include various isomers of butenes, various isomers of pentene, and various isomers of hexene, among others, for example.

Mixed $C_6$ streams useful in some embodiments disclosed herein may be produced by metathesis of $C_4$ streams, such as disclosed in U.S. Pat. No. 6,727,396, among others. For example, a mixture of internal and normal $C_6$ olefins may be produced during the metathesis of a mixed $C_4$ olefin stream, including isobutylene and normal butenes. In some embodiments, the metathesis reaction product may undergo one or more separation stages, such as to remove $C_2$-$C_5$ components, thus feeding a stream including primarily $C_6$ components (normal and iso-olefins) to processes disclosed herein.

In some embodiments, metathesis of a Raffinate II stream (i.e., a $C_4$ stream after butadiene and isobutylene removal) may produce isohexenes via reaction between 1-butene and any isobutene that may be present at concentrations of up to about 10% due to incomplete separation of the isobutylene from the $C_4$ feedstock.

Mixed $C_6$ streams useful in embodiments disclosed herein may also be produced by oligomerization of ethylene, such as ethylene dimerization and/or trimerization processes. Ethylene oligomerization may produce non-aromatic hydrocarbons, including $C_4$, $C_6$, $C_8$, and $C_{10}$ hydrocarbons, among others. In some embodiments, the oligomerization reaction product may undergo one or more separation stages, such as to remove $C_4$ and $C_{8+}$ components, thus feeding a stream including primarily $C_6$ components (normal and iso-olefins) to processes disclosed herein. Processes and catalysts for the oligomerization of ethylene are disclosed in, for example, U.S. Pat. Nos. 7,425,661, 7,414,006, 7,399,895, 7,384,886, 7,355,087, 7,273,959, 6,927,313, 6,743,960, 6,531,555, 5,811,618, 5,523,507, 5,968,866, 5,198,563, 4,538,018, 4,950,632, 5,105,048, 5,105,049, 5,166,114, and 6,455,648, among others. While oligomerization processes tend to produce primarily alpha olefins, some catalysts may include an isomerization functionality, increasing the isohexene present in the product. For example, dimerization processes for producing 2-butene may produce isohexenes as a reaction byproduct.

The oligomerization reaction, for example, can be performed in solution phase, slurry phase, gas phase or bulk phase. When the oligomerization is performed in solution or slurry phase, a diluent or solvent which is substantially inert under oligomerization conditions may be used. Suitable diluents or solvents are aliphatic and aromatic hydrocarbons, halogenated hydrocarbons, and olefins which are substantially inert under reaction conditions, such as those disclosed in US 2003/0166456. The oligomerization process may be performed in any one of a number of suitable reactors which are well known to one skilled in the art, including plug flow reactors (PFRs), continuous stirred tank reactors (CSTRs), fluidized bed reactors, fixed bed reactors, slurry reactors, boiling point reactors, and distillation column reactor systems, among others. Typically the oligomerization process of the present invention is carried out in a loop reactor operating in a continuous mode.

The oligomerization process may be performed under a range of process conditions known to one skilled in the art or disclosed in published literature such as, for example, those disclosed in US 2003/0166456. Typically, the temperature will be in the range from about −100° C. to about 200° C., preferably from about 0° C. to about 150° C., and more preferably from about 25° C., to about 100° C. Typically, the pressure will be in the range from about 0 to about 200 barg, preferably from about 1 to about 50 barg.

In some embodiments, the hydrocarbon feed streams may be derived from any source, and may include a concentration of <1 to 60 weight percent isohexenes, the balance being a mixture comprising normal hexenes, lighter hydrocarbons, such as $C_5$ components, and potentially heavier hydrocarbons, such as $C_7+$ components.

In some embodiments, the above described hydrocarbon streams containing mixed hexenes may be used directly, if lighter components are not present. In other embodiments, it may be desired to perform an initial fractionation of the hydrocarbon stream to separate $C_5$ and lighter components form the $C_6$ and heavier components. Initial fractionation of the $C_5$ and lighter components may be desired, for example, to limit the amount of light components in the resulting 1-hexene product, such as to meet product specifications for 1-hexene purity.

Alcohols useful in embodiments disclosed herein may include $C_1$ to $C_6$ primary and secondary alcohols. The term "alcohol" includes lower alkyl alcohols capable of forming azeotropes with the saturated and unsaturated hydrocarbons, in particular the $C_3$ to $C_7$ hydrocarbons, of the hydrocarbon feedstock. Examples of alcohols useful in embodiments disclosed herein include methanol, ethanol, n-propanol, i-propanol, n-butanol, i-butanol and t-butanol. In some embodiments, the alcohol may be methanol. In other embodiments, methanol may be used in combination with one or more of the $C_2+$ alcohols.

A mixed $C_6$ feed and alcohol may be contacted with a suitable catalyst to convert at least a portion of the iso-hexene in the feed to an ether, such as a C7 or C8 ether. The etherification reaction may be performed in any one of a number of suitable reactors which are well known to one skilled in the art, including plug flow reactors (PFRs), continuous stirred tank reactors (CSTRs), fluidized bed reactors, fixed bed reactors, slurry reactors, boiling point reactors, and catalytic distillation reactor systems, among others. Typically the etherification is carried out in a continuous mode.

The etherification reaction may be performed under a range of process conditions, such as at temperatures in the range from about 60° C. to about 100° C., where the pressure of the reactor may depend upon the type of reactor and the desired phase (liquid or vapor) at which reaction occurs. For example, in some embodiments, the pressure may be sufficient to maintain the reactants and products in the liquid phase. Determination of the required pressure is well within the skill of one in the art.

Alcohol may be fed to the reactor at a molar rate equal to or in excess of the molar rate of the iso-hexene in the feed. For example, methanol may be fed to the reactor at a rate in the range from about 1 to about 1.5 times the molar rate of the isohexene. In other embodiments, methanol may be fed to the reactor at a rate in the range from about 1.1 to about 1.3 times the molar rate of the isohexene, such as about 1.2 times the molar rate of the isohexene fed to the reactor. Use of excess alcohol may be preferred, such as to shift the equilibrium of the reaction further to the ether product. Conversion of iso-hexene at conditions disclosed herein may be in excess of 90% (molar). The reaction of normal hexenes with methanol or other alcohols are negligible.

Any catalyst typically used in etherification processes may be used in embodiments disclosed herein. Conventional cation exchange resins and/or zeolites may be used in various embodiments. Thus, the resin may contain sulfonic acid groups and may be obtained by polymerization or copolymerization of aromatic vinyl compounds followed by sulfonation. Examples of aromatic vinyl compounds suitable for preparing polymers of copolymers include: styrene, vinyl toluene, vinyl naphthalene, vinyl ethyl-benzene, methyl styrene, vinyl chlorobenzene and vinyl xylene. The acid cation exchange resin may contain some 1.3 to 1.9 sulfonic acid groups per aromatic nucleus. In some embodiments, resins may be based on copolymers of aromatic monovinyl compounds with aromatic polyvinyl compounds in which the polyvinyl benzene content is from about 1 to 20 weight percent of the copolymer. The ion exchange resin may have a granular size of about 0.15 to 1 mm in some embodiments. In addition to the above resins, perfluorosulfonic acid resins, which are copolymers of sulfonyl fluorovinyl ethyl and fluorocarbon, may be used.

The catalysts useful in the etherification processes disclosed herein may contain a zeolite sometimes referred to as medium pore or ZSM-5 type. In other embodiments, the zeolite may be a medium pore shape selective acidic metallosilicate zeolite selected from the group consisting of ZSM-5, ZSM-11, ZSM-12, ZSM-22, ZSM-23, ZSM-35, ZSM-50, MCM-22, as well as larger pore zeolite Y and zeolite Beta. The original cations associated with zeolites utilized herein may be replaced by a wide variety of other cations according to techniques well known in the art, e.g., by ion exchange. Typical replacing cations include hydrogen, ammonium, alkyl ammonium, and metal cations, and their mixtures. In the case of metal cations, metals of Groups IB to VIIIA of the Periodic Table, including, by way of example, iron, nickel, cobalt, copper, zinc, palladium, calcium, chromium, tungsten, molybdenum, rare earth metals, etc. may be used. These metals may also be present in the form of their oxides.

In other embodiments, etherification catalysts for the isoalkene reactants include mineral acids such as sulfuric acid, boron trifluoride, phosphoric acid on kieselguhr, phosphorous-modified zeolites, heteropoly acids, and various sulfonated resins. These resin type catalysts may include the reaction products of phenolformaldehyde resins and sulfuric acid and sulfonated polystyrene resins including those crosslinked with divinylbenzene. A particular etherification catalyst is a macroporous acid-form of a sulfonic ion exchange resin such as a sulfonated styrene-divinylbenzene resin, as described in U.S. Pat. No. 2,922,822, having a degree of crosslinking of about 5 to 60%. Specialized resins have been described in the art and include copolymers of sulfonyl fluorovinyl ether and fluorocarbons, as described in U.S. Pat. No. 3,489,243. Another specially prepared resin consists of $SiO_2$-modified cation exchangers described in U.S. Pat. No. 4,751,343. The macroporous structure of a suitable resin is described in detail in U.S. Pat. No. 5,012,031 as having a surface area of at least about 400 m$^2$/g, a pore volume of about 0.6 to 2.5 ml/g, and a mean pore diameter of 40 to 1000 Angstroms. It is contemplated that the subject process could be performed using a metal-containing resin which contains one or more metals from sub-groups VI, VII or VIII of the Periodic Table such as chromium, tungsten, palladium, nickel, chromium, platinum, or iron as described in U.S. Pat. No. 4,330,679. Further information on suitable etherification catalysts may be obtained by reference to U.S. Pat. Nos. 2,480,940, 2,922,822, and 4,270,929.

Where the etherification step of the present invention is practiced in a catalytic distillation process, the catalytic material may be in any form which permits its incorporation into a distillation tower, such as a fixed bed, but may also be in a form which serves as a distillation packing, for example, rings, saddles, balls, irregular pieces, sheets, tubes, spirals, packed in bags, plated on grills or screens, and reticulated polymer foams. In some embodiments, a catalytic distillation structure for use herein includes placing the cation exchange resin particles into a plurality of pockets in a cloth belt, which is supported in the distillation column reactor by open mesh knitted stainless steel wire by twisting the two together in a helical form. This allows the requisite flows and prevents loss of catalyst. The cloth may be any material which is inert in the reaction, such as cotton, linen, fiber glass cloth, or TEFLON. U.S. Pat. Nos. 4,302,356, 4,443,559, and 5,730,843 disclose catalyst structures which are useful as distillation structures, and are incorporated herein by reference.

As described above, the etherification of isohexene may be performed in any number of reactors. When performed in a catalytic distillation reactor system, the resulting ethers ($C_{7+}$ ethers) may be concurrently separated from the normal hexenes and hexanes. When the etherification reaction is performed in non-distillative reactor, such as a fixed bed reactor, for example, the etherification reactor effluent may be fed to a distillation column to separate the heavy $C_{7+}$ ethers from the other components. The distillate product may contain normal hexenes, unreacted isohexene and alcohol, such as methanol. The heavy $C_{7+}$ ethers are recovered in the bottoms product. The etherification reaction could also take place in reactors located on side draws from the distillation column. In some embodiments, there can be a multiplicity of such side draw reactors along the length of a distillation column to allow for maximum etherification conversion.

In some embodiments, it may be desired to enhance the conversion of isohexene, such as via a second stage "trim" reactor. Due to the initial separation of the $C_7$+ ethers from the isohexene and alcohol, the equilibrium has shifted to the product, and additional reaction between isohexene and alcohol may occur. The trim reactor, for example, may be integrated with the overhead system of the distillation column, or may be incorporated into the distillation column above the effluent feed point. Trim reactors may include distillation column reactor systems, fixed bed reactors, and other types of reactors known in the art. The choice of the number of etherification reaction stages will depend upon the concentration of isohexenes in the feed stream and the desired purity of the 1-hexene product.

Oxygenates contained in the overhead product of the etherification separations may act as poisons to the isomerization catalysts used in downstream reactors. As a result, it is desired to remove all or substantially all of the oxygenates, such as any ethers carried over, unreacted alcohols, etc., from the normal hexenes.

The distillate product from the ether separation column, for example, may contain up to about 2 weight percent isohexene, up to about 5 weight percent alcohol, and about 90 to 95 weight percent normal hexenes. The alcohol should be removed from this stream prior to feeding the stream to the $C_6$ isomerization system.

The distillate product may be contacted with water in a water wash system to remove the alcohol, such as methanol. In some embodiments, the water wash system may consist of 1 or more wash stages. For example, the water wash system may be a two-stage water wash system, where the first stage is operated at a water flow rate up to about 20 times the methanol rate in the $C_6$ feed, removing at least 90% of the methanol. The second stage of the water wash system may be operated at a water flow rate up to about 100 or 150 times the methanol rate in the $C_6$ feed, again removing at least 90% of the methanol. The $C_6$ product from the water wash system may contain less than about 0.05 weight percent (500 ppm) alcohol in some embodiments. In other embodiments, the $C_6$ product from the water wash system may contain less than about 0.015 weight percent (150 ppm) alcohol.

Any ethers carried over into the distillate product recovered from the ether separation column will also be removed in the water wash system. The $C_6$ product from the water wash system may contain less than about 0.05 weight percent (500 ppm) $C_{7+}$ ethers in some embodiments. In other embodiments, the $C_6$ product from the water wash system may contain less than about 0.015 weight percent (150 ppm) $C_{7+}$ ethers.

The ethers and alcohols in the $C_6$ product stream from the water wash system may be contacted with a solid adsorbent to remove additional oxygenates, ethers and alcohols, in the $C_6$ product stream. For example, the $C_6$ product stream may be fed to a guard bed containing zeolites or other appropriate absorbents to remove alcohols, ethers, and/or water.

The treated $C_6$ product, including 1-hexene, 2-hexenes, and 3-hexenes, may then be isomerized in the presence of a suitable catalyst. The reaction can take place either in the liquid phase or the vapor phase.

Useful isomerization catalysts may include basic metal oxides such as magnesium oxide, calcium oxide, barium oxide, and lithium oxide, either individually or in combination. Other oxides, such as sodium oxide or potassium oxide may be incorporated into the catalyst as promoters. In certain embodiments, the catalyst for use in isomerization may be magnesium oxide (MgO). While certain aspects will be described herein in terms of magnesium oxide, it should be understood that the other basic metal oxides mentioned above are also contemplated as being within the scope of embodiments disclosed herein. The isomerization catalysts according to embodiments disclosed herein may be in the form of pellets, extrudates, and the like. In embodiments disclosed herein, the catalyst may be contacted with the reactants in the absence of added hydrogen (i.e., not a hydroisomerization process), as this may favor the formation of internal olefins.

For vapor phase reaction, such catalysts include, but are not limited to, basic metal oxides, including magnesium oxide. The equilibrium of mixed hexenes to form 1-hexene is favored by higher temperatures, hence the vapor phase reaction occurring at higher temperatures is preferred.

The 2-hexenes and 3-hexenes may be isomerized to 1-hexene at a weight hourly space velocity (WHSV) in the range from about 3 to about 200, preferably from about 10 to about 60. The isomerization reaction may be carried out at a pressure in the range from about 2 bar to about 40 bar, preferably from about 3 bar to about 10 bar, and at a temperature in the range from about 40° C. to about 300° C., preferably from about 60° C. to about 150° C. for liquid phase and from about 300° C. to about 400° C. for vapor phase reaction.

For example, the treated $C_6$ product stream may then be sent to a $C_6$ isomerization system to convert internal hexene olefins to 1-hexene. The $C_6$ product from the treaters (water wash and/or adsorbent systems) may be mixed with recycled internal hexenes (2-hexenes and 3-hexenes) from a downstream separation system and vaporized in a steam heated heater. The vaporized C6 stream may exchange heat with the hot isomerization reactor product. The isomerization reactor feed may be further heated to reaction temperature inside a fuel-fired furnace prior to being fed to the reactor.

The isomerization reactor product is an equilibrium mixture of 1-hexene, 2-hexenes and 3-hexenes, including their cis and trans isomers. This product mixture may then be separated in a hexene separation system, such as via distillation, to produce polymer grade 1-hexene as a distillate product. The bottoms product, 2-hexenes and 3-hexenes, may be recycled to the isomerization reactor. A small purge may be taken from the separation system to remove inert components from the $C_6$ isomerization system.

In some embodiments, it may be desired to further process or use the ethers formed during the hexene upgrading processes disclosed herein. For example, the ethers may be used as a blending component for gasoline or diesel fuels.

In other embodiments, it may be desired to backcrack the ethers to form a pure isohexene product. The ethers may be contacted with an acidic ion exchange resin at appropriate reaction conditions to crack the ether to form isohexene and an alcohol. The isohexene may then be separated from the alcohol via distillation, resulting in a high purity isohexene product.

Figure 1:
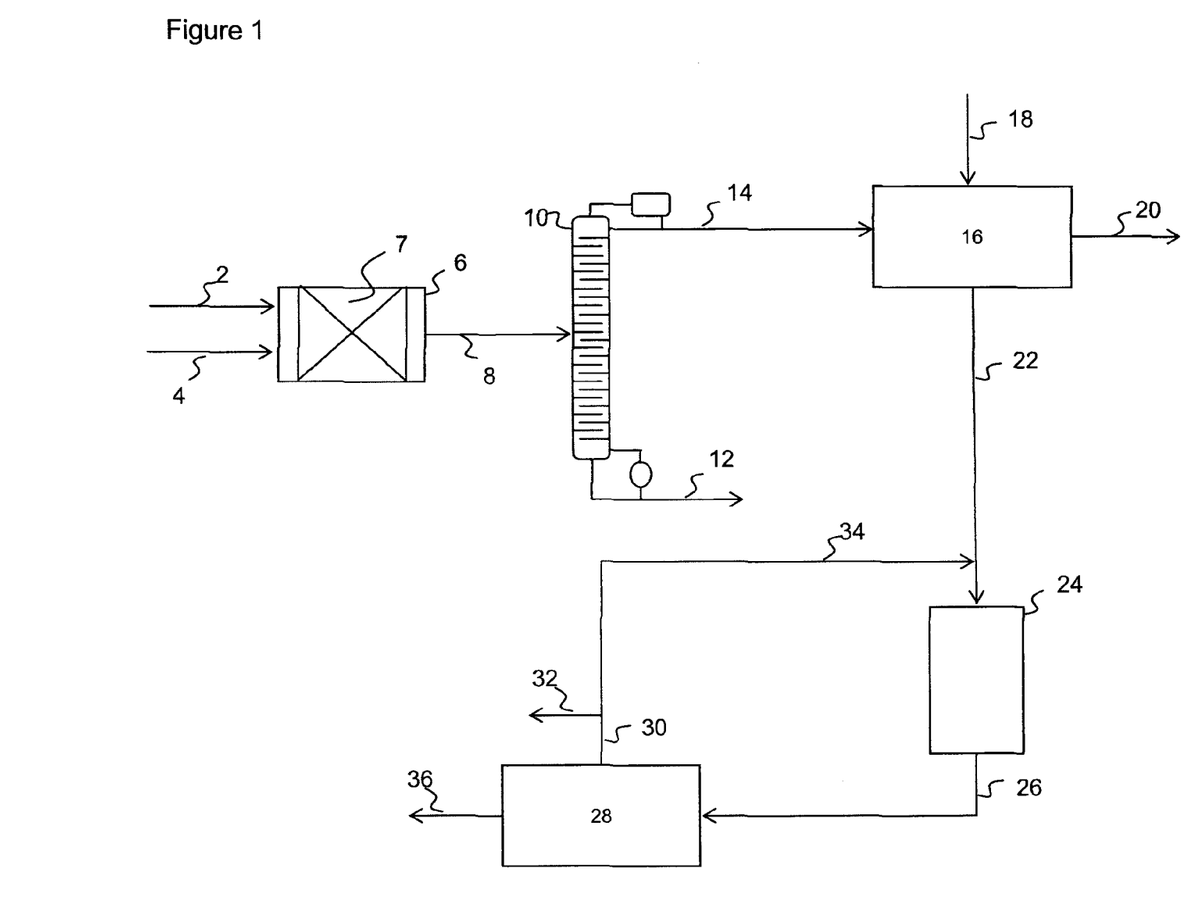
FIG. 1 is a simplified flow diagram of a process for upgrading a mixed hexene stream according to embodiments disclosed herein.
Figure 2:
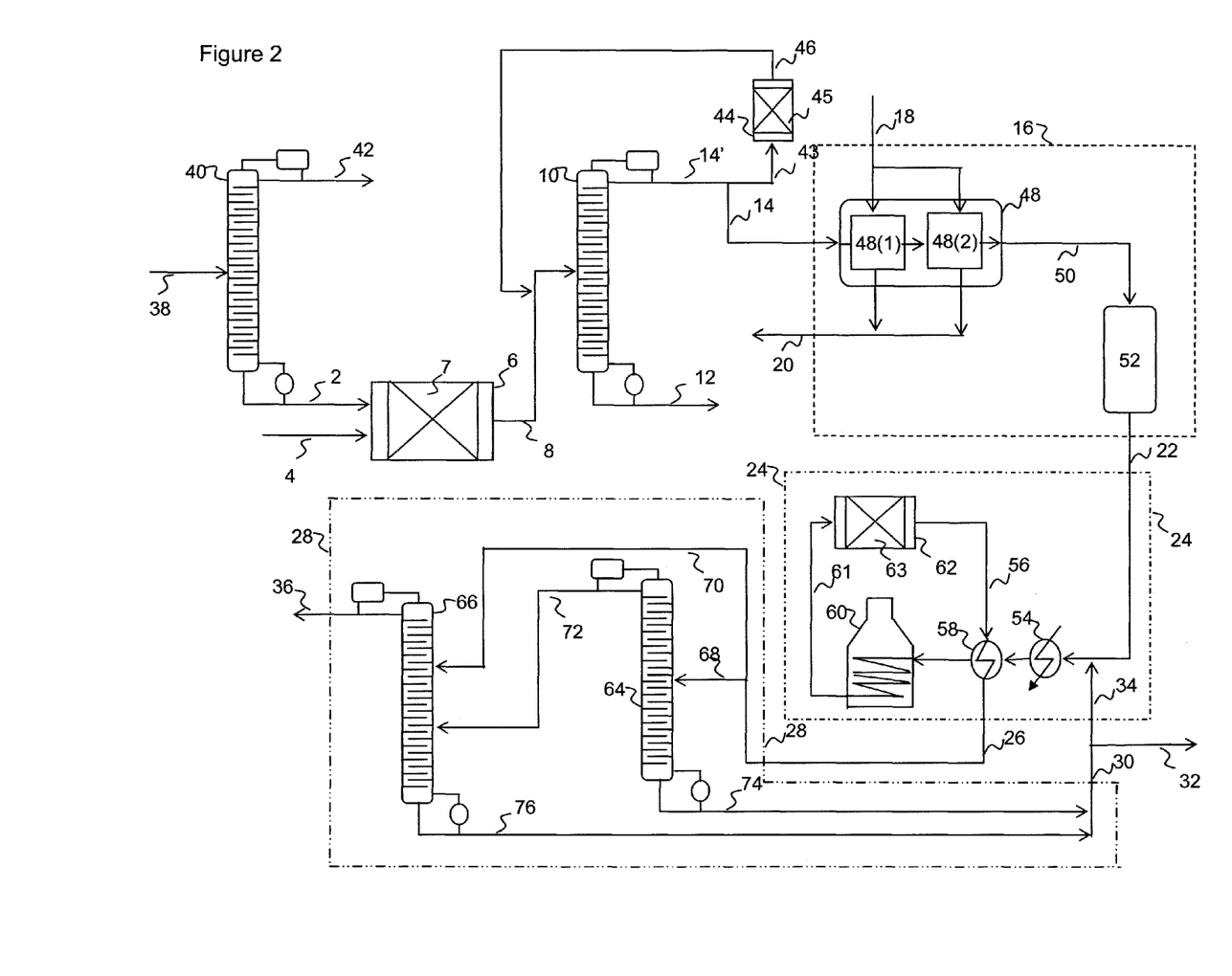
FIG. 2 is a simplified flow diagram of a process for upgrading a mixed hexene stream according to embodiments disclosed herein.
Figure 3:
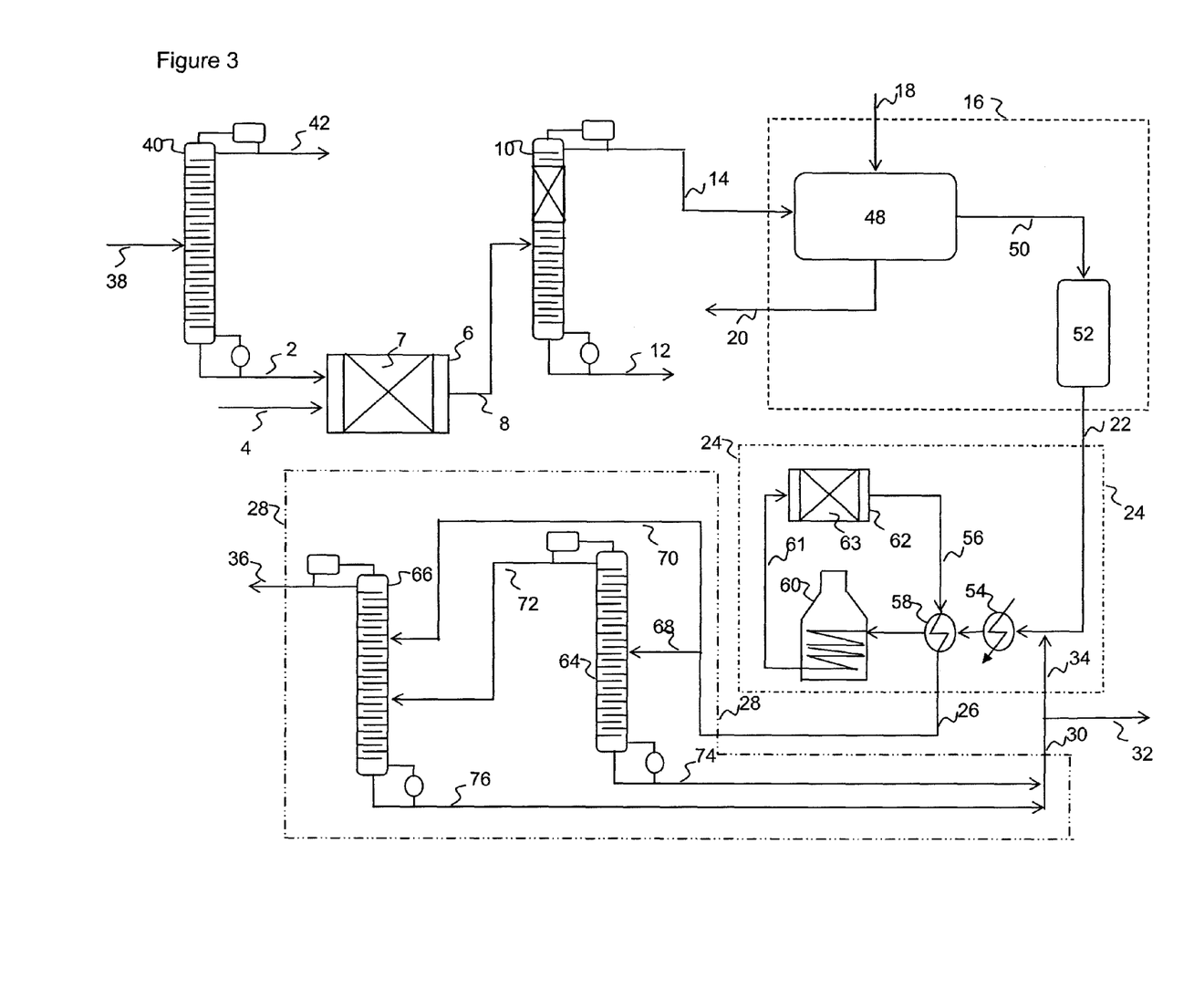
FIG. 3 is a simplified flow diagram of a process for upgrading a mixed hexene stream according to embodiments disclosed herein.

As described above, various apparatus and flow schemes may be used to upgrade a mixed hexene stream to 1-hexene according to embodiments disclosed herein. Several of these flow schemes are illustrated in FIGS. 1-3, described below. While only a few flow schemes have been presented, other process flow schemes may be used according to embodiments disclosed herein.

Referring now to FIG. 1, a simplified flow diagram of a process for upgrading a mixed hexene stream according to embodiments disclosed herein is illustrated. A mixed hydrocarbon stream, including isohexene and normal hexenes, and an alcohol, such as methanol, are fed via flow lines 2 and 4, respectively, to an etherification reactor 6. Reactor 6 contains one or more beds 7 of etherification catalyst, as described above, for converting at least a portion of the isohexene and methanol to $C_7$ ethers.

Effluent from etherification reactor 6 is then fed via flow line 8 to ether separation system 10, wherein the ethers are separated from the normal hexenes. The ethers, having a boiling point higher than the normal hexenes, may be recovered as a bottoms product via flow line 12. The normal hexenes, unreacted isohexenes, and unreacted methanol are recovered as an overheads product via flow line 14.

The overheads product is then processed to separate the methanol from the hexenes in oxygenate removal system 16. Oxygenate removal system 16 may include one or more of a water wash system and an oxygenate adsorbent system (not shown). For example, the overheads product may be contacted with water fed via flow line 18 to separate at least a portion of the methanol. The aqueous fraction, including water and extracted methanol, may be recovered via flow line 20, and the hydrocarbon fraction, including the normal hexenes and unreacted isohexene may be recovered from oxygenate removal system via flow line 22.

The hexenes in flow line 22, including 1-hexene, 2-hexene, and 3-hexene, may then be fed to an isomerization reactor system 24. Isomerization reactor system 24 may include, for example, a heater (not shown) and a reactor (not shown) including one or more beds of isomerization catalyst and operated at conditions suitable for converting at least a portion of the internal olefins (2-hexenes and 3-hexenes) to 1-hexene.

Effluent from the isomerization reactor system 24 may be recovered via flow line 26 and fed to a 1-hexene recovery system 28. 1-hexene recovery system 28, for example, may include one or more distillation columns for the separation of the 1-hexene from the 2-hexenes and 3-hexenes. 2-hexene and 3-hexene may be recovered from recovery system 28 via flow line 30, a portion of which may be purged via flow line 32, and a portion of which may be recycled to isomerization reactor 24 via flow line 34. 1-hexene product may be recovered from 1-hexene recovery system 28 via flow line 36.

Referring now to FIG. 2, a simplified flow diagram of a process for upgrading a mixed hexene stream according to embodiments disclosed herein is illustrated, where like numerals represent like parts. In this embodiment, an initial $C_5$ separation and a trim reactor are used, and various apparatus that may be used in the oxygenate removal system, isomerization reactor system, and the 1-hexene recovery system are illustrated.

A mixed hydrocarbon stream, such as a light cracked naphtha or an ethylene oligomerization product stream and including $C_5$ components and mixed hexenes, is fed via flow line 38 to a depentanizer 40. The mixed hydrocarbons are separated in the depentanizer, where the $C_5$ and lighter components are recovered as an overheads fraction 42, and the $C_6$ and heavier components, if any, are recovered as a bottoms fraction. The bottoms fraction may then be forwarded via flow line 2 as a mixed hexene stream to etherification reactor 6.

Following separation of the ethers from the normal hexenes, unreacted methanol, and unreacted isohexene in ether separation system 10, a portion of the overhead fraction 14' may be fed via flow line 43 to trim reactor 44, which contains at least one bed of etherification catalyst 45. Trim reactor 44 may provide additional conversion of isohexene and alcohol, due to the removal of ethers in separator 10 and the resultant shift in equilibrium. Effluent from trim reactor 44 may be fed via flow line 46 back to etherification separation system 10 to separate the additional ethers produced. The remainder of the overhead fraction may be fed via flow line 14 to oxygenate removal system 16.

As illustrated in FIG. 2, oxygenate removal system 16 may include a water wash system 48, where the overhead fraction, including methanol and hexenes, may be contacted with water fed via flow line 18 to remove at least a portion of the methanol. Water wash system 48 may be a two stage system, including first wash stage 48(1) and second wash stage 48(2), where the hydrocarbon phase may be contacted with water at the same or different flow rates to achieve the desired alcohol and ether removal. The resultant hexene stream, depleted in methanol and any ethers that may have carried over in the overheads fraction, may then be fed via flow line 50 to treater 52, where the stream may be contacted with an adsorbent, thus removing additional ethers, alcohols, and any water that may be present.

The mixed hexenes, having essentially no oxygenates, may then be fed via flow line 22 to isomerization reaction system 24. The $C_6$ product from the treater 52 may be mixed with recycled 2-hexenes and 3-hexenes from the 1-hexene recovery system 28, and fed to a steam heater 54 to vaporize at least a portion of the hexenes. The vaporized $C_6$ stream may then exchange heat with the hot isomerization reactor effluent 56 in heat exchanger 58. The isomerization reactor feed is further heated to reaction temperature via a fuel-fired furnace 60 and fed via flow line 61 to isomerization reactor 62. Isomerization reactor 62 may include at least one bed 63 of an isomerization catalyst, such as magnesium oxide tablets, for converting at least a portion of the 2-hexenes and 3-hexenes to 1-hexene. The effluent from isomerization reactor 62 may include an equilibrium mixture of 1-hexene, 2-hexenes, and 3-hexenes, including their cis- and trans-isomers. This product, as noted above, may be cooled via indirect heat exchange with the isomerization reactor feed, and then may be fed to 1-hexene recovery system 28.

In the 1-hexene recovery system 28, the separation of 1-hexene is carried out with two inter-linked separation towers, 64, 66. The feed to the separation towers 64, 66 is split; one portion is fed via flow line 68 to the first tower 64, and the other portion is fed via flow line 70 to the second tower 66. The distillate product stream 72 from the first tower is enriched in 1-hexene content, and the bottoms product 74 contains 2-hexenes and 3-hexenes. The distillate 72 from the first tower is fed to the second tower 66 at a stage above the feed 70. The bottoms products from each of the first and second towers, flow lines 74 and 76, respectively, are mixed and recycled to the hexene isomerization reactor via flow line 30. A high purity 1-hexene product is recovered from the second tower 66 via flow line 36.

In some embodiments, second tower 66 may be operated at a lower pressure than the first tower. This enables the condenser of the first tower 64 to be at a higher temperature than the reboiler of the second tower 66, allowing heat integration and savings on system utility requirements. The duties of the condenser and reboiler may be balanced, in some embodiments, by the split of the feed to the towers. Thus, the heat integration is achieved by linking the condenser from the first tower 64 with the reboiler of the second tower 66.

Referring now to FIG. 3, a simplified flow diagram of a process for upgrading a mixed hexene stream according to embodiments disclosed herein is illustrated, where like numerals represent like parts. In this embodiment, ether separation column 10 and trim reactor 44 are combined in a distillation column reactor system 80. Due to the internal separation of ethers from unreacted alcohol and isohexene, similar benefits to that obtained with a trim reactor may be obtained using a distillation column reactor system containing a bed 82 of etherification catalyst in the upper portion of the column. Further embodiments disclosed herein may utilize a catalytic distillation column alone, without an initial fixed bed reactor, with all of the etherification reactions taking place within the catalytic distillation reaction system.

Hexene upgrading processes disclosed herein may allow for efficient production, separation, and/or recovery of 1-hexene at a high purity. For example, 1-hexene product streams recovered in embodiments disclosed herein may have a 1-hexene content of at least 98 weight percent; at least 98.5 weight percent in other embodiments; at least 99 weight percent in other embodiments; and at least 99.5 weight percent in yet other embodiments.

EXAMPLES

The following examples are derived from modeling techniques and although the work was actually achieved, the inventors do not present these examples in the past tense to comply with applicable rules.

Example 1

A hexene upgrading process similar to that shown in FIG. 2 is simulated, where the initial mixed hexene feed to the process, stream 38, contains $C_5$s and $C_6$s, and other components as shown in the mass balance (Table 2). The mixed hexene stream 38 is fed to depentanizer 40, details of which are given in tower specifications Table 1.

The alcohol feed to the etherification reactor is methanol, and is fed to the etherification reactor 6 at a rate specified at 1.2 times the molar rate of isohexene in the reactor feed. The etherification reactor is a liquid phase reactor operating at 80° C., and the reaction rate constants for the reaction of various hexene isomers, such as 2-methyl-2-pentene, trans-3-methyl-2-pentene, and cis-3-methyl-3-pentene, are estimated based on Gibbs Free Energy (simulation option). At the reaction temperature, conversion of isohexene to the ether is above 90 percent, as may be ascertained from the mass balance (Table 2). The reaction rates of normal hexenes with methanol are negligible, and are not considered in the process.

The etherification reaction product enters ether column 10 to separate the heavy C7 ether (boiling point of 101° C.) from the other components. Specifics of ether column 10 are also given in Table 1. The distillate product 14' contains normal hexenes, and unreacted isohexene and methanol. The ether is recovered in the bottoms product 12.

A second stage trim reactor 44 is used to obtain further conversion of isohexene components. As the C7 ether is removed from the trim reactor feed, equilibrium is shifted to the right, and additional reaction between isohexene and methanol takes place. The trim reactor product 46 is fed to the ether column 10 to remove the additional C7 ether produced.

A portion of the ether column 10 distillate 14', free of C7 ether, is taken to the oxygenate removal step via flow line 14. The distillate produced from the ether column contains approximately 2 weight percent isohexene, 4.1 weight percent methanol, and about 93 weight percent normal hexenes. The methanol is removed by a two-stage water wash unit. In the first stage wash, a water flow rate of 10 times the methanol in the C6 feed is used, recovering about 94% of the methanol. In the second stage wash, a water flow rate of 100 times the methanol in the C6 feed is used, recovering about 93% of the methanol remaining after the first stage wash. The C6 product from the second stage wash contains about 130 ppm methanol and about 150 ppm ether. The methanol and ether are then removed from the C6 product stream 50 in a treater filled with solid adsorbents. The treated C6 stream, containing about 2.1 weight percent isohexene, 97.2 weight percent normal hexenes, and 0.6 weight percent normal hexane, is then fed to isomerization section 24 to make 1-hexene.

The C6 product from the treater is mixed with recycled 2-hexenes from the C separation system and vaporized in a steam heater. The vaporized C6 stream exchanges heat with the hot isomerization reactor product. The isomerization reactor feed is further heated to the reaction temperature inside a fuel-fired furnace 60. The isomerization reactor operates at 650° F. and 56 psia, and the catalyst is magnesium oxide tablets. The reactor product is an equilibrium mixture of 1-hexene, 2-hexenes, and 3-hexenes.

The isomerization product mixture is then separated using a split tower system as illustrated in FIG. 2. Column details are given in Table 1. The product 1-hexene is removed as a distillate from the second tower, and has a 1-hexene content of about 98.3 weight percent.

TABLE 1

Tower Specifications.

| Specifications | Depentanizer 40 | Ether Column 10 | First Hexene Splitter 64 | Second Hexene Splitter 66 |
|---|---|---|---|---|
| No. of stages | 40 | 30 | 80 | 70 |
| Feed stage | 12 | 10/15 | 25 | 40/60 |
| Condenser Pressure (kPa) | 600 | 200 | 217 | 117 |
| Reboiler Pressure (kPa) | 700 | 300 | 263 | 158 |
| Condenser Temperature (° C.) | 98.3 | 87.4 | 90.9 | 66.8 |
| Reboiler Temperature (° C.) | 147.9 | 143.4 | 102 | 82.5 |
| Reflux Ratio | 3.7 | 1.7 | 49 | 49 |
| Top Specification | 0.5 mole % (n-C6 + iso-C6) | 0.01 mole % C7 Ether | 50 mole % 2- and 3-hexene | 0.75 mole % 2- and 3-hexene |
| Bottom Specification | 0.01 mole % n-C5 | 0.01 mole % C6 (total) | 1 mole % 1-hexene | 2.5 mole % 1-hexene |

TABLE 2

Unit Mass Balance

| Component | | Stream | | | | | | | |
|---|---|---|---|---|---|---|---|---|---|
| | | 38 | 42 | 2 | 4 | 8 | 14' | 14 | 43 |
| Water | Wt. % | 0.0 | 0.0 | 0.0 | 0.0 | 0.0 | 0.0 | 0.0 | 0.0 |
| n-butane | Wt. % | 0.1 | 0.4 | 0.0 | 0.0 | 0.0 | 0.0 | 0.0 | 0.0 |
| Trans-2-butene | Wt. % | 0.2 | 0.6 | 0.0 | 0.0 | 0.0 | 0.0 | 0.0 | 0.0 |
| Cis-2-butene | Wt. % | 0.3 | 1.2 | 0.0 | 0.0 | 0.0 | 0.0 | 0.0 | 0.0 |
| n-pentane | Wt. % | 0.7 | 2.5 | 0.0 | 0.0 | 0.0 | 0.0 | 0.0 | 0.0 |
| 3-methyl-1-butene | Wt. % | 0.0 | 0.0 | 0.0 | 0.0 | 0.0 | 0.0 | 0.0 | 0.0 |
| Trans-2-pentene | Wt. % | 14.1 | 53.9 | 0.0 | 0.0 | 0.0 | 0.0 | 0.0 | 0.0 |
| 1-pentene | Wt. % | 1.9 | 7.1 | 0.0 | 0.0 | 0.0 | 0.0 | 0.0 | 0.0 |
| Cis-2-pentene | Wt. % | 8.8 | 33.7 | 0.0 | 0.0 | 0.0 | 0.0 | 0.0 | 0.0 |
| 1-hexene | Wt. % | 0.7 | 0.0 | 1.0 | 0.0 | 0.8 | 1.5 | 1.5 | 1.5 |
| Trans-2-hexene | Wt. % | 14.6 | 0.2 | 19.7 | 0.0 | 16.9 | 31.1 | 31.1 | 31.1 |
| Trans-3-hexene | Wt. % | 8.8 | 0.1 | 11.8 | 0.0 | 10.1 | 18.6 | 18.6 | 18.6 |
| Cis-2-hexene | Wt. % | 18.3 | 0.1 | 24.7 | 0.0 | 21.1 | 38.9 | 38.9 | 38.9 |
| Cis-3-hexene | Wt. % | 1.5 | 0.0 | 2.0 | 0.0 | 1.7 | 3.1 | 3.1 | 3.1 |
| 2-methyl-2-pentene | Wt. % | 2.9 | 0.0 | 4.0 | 0.0 | 0.9 | 0.8 | 0.8 | 0.8 |
| 2-methyl-1-pentene | Wt. % | 0.0 | 0.0 | 0.0 | 0.0 | 0.0 | 0.0 | 0.0 | 0.0 |
| 4-methyl-1-pentene | Wt. % | 0.0 | 0.0 | 0.0 | 0.0 | 0.0 | 0.0 | 0.0 | 0.0 |
| 4-methyl-cis-2-pentene | Wt. % | 0.0 | 0.0 | 0.0 | 0.0 | 0.0 | 0.0 | 0.0 | 0.0 |
| 4-methyl-trans-2-pentene | Wt. % | 0.0 | 0.0 | 0.0 | 0.0 | 0.0 | 0.0 | 0.0 | 0.0 |
| 3-methyl-cis-2-pentene | Wt. % | 11.7 | 0.1 | 15.8 | 0.0 | 0.5 | 0.4 | 0.4 | 0.4 |
| 3-methyl-trans-2-pentene | Wt. % | 14.6 | 0.0 | 19.8 | 0.0 | 0.8 | 0.8 | 0.8 | 0.8 |
| Methanol | Wt. % | 0.0 | 0.0 | 0.0 | 100.0 | 2.7 | 4.1 | 4.1 | 4.1 |
| C7 Ether | Wt. % | 0.0 | 0.0 | 0.0 | 0.0 | 43.2 | 0.0 | 0.0 | 0.0 |
| n-hexane | Wt. % | 0.3 | 0.0 | 0.4 | 0.0 | 0.3 | 0.6 | 0.6 | 0.6 |
| Trans-3-octene | Wt. % | 0.6 | 0.0 | 0.8 | 0.0 | 0.7 | 0.0 | 0.0 | 0.0 |
| Sum | Wt. % | 100 | 100 | 100 | 100.0 | 100 | 100 | 100 | 100 |
| Stream Flow Rate | Kg/h | 9600 | 2509 | 7091 | 1218 | 8309 | 11252 | 4501 | 6751 |

| Component | | Stream | | | | | | | |
|---|---|---|---|---|---|---|---|---|---|
| | | 46 | 50 | 22 | 34 | 22 + 34 | 26 | 32 | 36 |
| Water | Wt. % | 0.0 | 0.0 | 0.0 | 0.0 | 0.0 | 0.0 | 0.0 | 0.0 |
| n-butane | Wt. % | 0.0 | 0.0 | 0.0 | 0.0 | 0.0 | 0.0 | 0.0 | 0.0 |
| Trans-2-butene | Wt. % | 0.0 | 0.0 | 0.0 | 0.0 | 0.0 | 0.0 | 0.0 | 0.0 |
| Cis-2-butene | Wt. % | 0.0 | 0.0 | 0.0 | 0.0 | 0.0 | 0.0 | 0.0 | 0.0 |
| n-pentane | Wt. % | 0.0 | 0.0 | 0.0 | 0.0 | 0.0 | 0.0 | 0.0 | 0.0 |
| 3-methyl-1-butene | Wt. % | 0.0 | 0.0 | 0.0 | 0.0 | 0.0 | 0.0 | 0.0 | 0.0 |
| Trans-2-pentene | Wt. % | 0.0 | 0.0 | 0.0 | 0.0 | 0.0 | 0.0 | 0.0 | 0.0 |
| 1-pentene | Wt. % | 0.0 | 0.0 | 0.0 | 0.0 | 0.0 | 0.0 | 0.0 | 0.0 |
| Cis-2-pentene | Wt. % | 0.0 | 0.0 | 0.0 | 0.0 | 0.0 | 0.0 | 0.0 | 0.0 |
| 1-hexene | Wt. % | 1.5 | 1.6 | 1.6 | 1.5 | 1.5 | 7.4 | 1.5 | 98.3 |
| Trans-2-hexene | Wt. % | 31.1 | 32.4 | 32.4 | 40.6 | 40.0 | 38.1 | 40.6 | 0.3 |
| Trans-3-hexene | Wt. % | 18.6 | 19.4 | 19.4 | 18.9 | 19.0 | 17.8 | 18.9 | 0.2 |
| Cis-2-hexene | Wt. % | 38.9 | 40.6 | 40.6 | 20.3 | 21.8 | 19.1 | 20.3 | 0.0 |
| Cis-3-hexene | Wt. % | 3.1 | 3.2 | 3.2 | 6.2 | 6.0 | 5.9 | 6.2 | 0.3 |

TABLE 2-continued

Unit Mass Balance

| | | | | | | | | | | |
|---|---|---|---|---|---|---|---|---|---|---|
| 2-methyl-2-pentene | Wt. % | 0.1 | 0.8 | 0.8 | 0.2 | 0.2 | 0.1 | 0.2 | 0.0 |
| 2-methyl-1-pentene | Wt. % | 0.0 | 0.0 | 0.0 | 0.0 | 0.0 | 0.0 | 0.0 | 0.5 |
| 4-methyl-1-pentene | Wt. % | 0.0 | 0.0 | 0.0 | 0.0 | 0.0 | 0.0 | 0.0 | 0.0 |
| 4-methyl-cis-2-pentene | Wt. % | 0.0 | 0.0 | 0.0 | 0.0 | 0.0 | 0.0 | 0.0 | 0.2 |
| 4-methyl-trans-2-pentene | Wt. % | 0.0 | 0.0 | 0.0 | 0.0 | 0.0 | 0.0 | 0.0 | 0.2 |
| 3-methyl-cis-2-pentene | Wt. % | 0.1 | 0.4 | 0.4 | 2.6 | 2.4 | 2.4 | 2.6 | 0.0 |
| 3-methyl-trans-2-pentene | Wt. % | 0.1 | 0.9 | 0.9 | 5.6 | 5.3 | 5.3 | 5.6 | 0.0 |
| Methanol | Wt. % | 3.4 | 0.0 | 0.0 | 0.0 | 0.0 | 0.0 | 0.0 | 0.0 |
| C7 Ether | Wt. % | 2.3 | 0.0 | 0.0 | 0.0 | 0.0 | 0.0 | 0.0 | 0.0 |
| n-hexane | Wt. % | 0.6 | 0.6 | 0.6 | 3.9 | 3.7 | 3.7 | 3.9 | 0.0 |
| Trans-3-octene | Wt. % | 0.0 | 0.0 | 0.0 | 0.0 | 0.0 | 0.0 | 0.0 | 0.0 |
| Sum | Wt. % | 100 | 100 | 100 | 100 | 100 | 100 | 100 | 100 |
| Stream Flow Rate | Kg/h | 6751 | 4318 | 4316 | 56091 | 60407 | 60407 | 567 | 3696 |

As described above, embodiments disclosed herein may provide for efficient production and separation of 1-hexene from a mixed hexene stream including isohexenes, 2-hexenes, and 3-hexenes. Advantageously, embodiments disclosed herein may provide for one or more of the following: lower utility costs associated with production and/or recovery of 1-hexene; higher purity 1-hexene (e.g., less isohexene content, among others); and higher 1-hexene yields, among other benefits.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for upgrading a mixed hexene stream, the process comprising:
    feeding an alcohol and a mixed hydrocarbon stream comprising isohexene, 2-hexene, and 3-hexene to an etherification reaction zone containing an etherification catalyst;
    contacting the isohexene and the alcohol in the presence of the etherification catalyst at reaction conditions of temperature and pressure to convert at least a portion of the isohexene and the alcohol to an ether;
    recovering an effluent from the etherification reactor comprising ether, 2-hexene, 3-hexene, and unreacted alcohol and isohexene;
    separating the etherification reactor effluent in a first distillation system to recover a bottoms fraction comprising the ether and an overheads fraction comprising the 2-hexene, 3-hexene, and the unreacted alcohol and isohexene;
    feeding at least a portion of the overheads fraction to an isomerization reaction zone containing an isomerization catalyst;
    contacting the 2-hexene and 3-hexene with the isomerization catalyst at conditions of temperature and pressure to convert at least a portion of the 2-hexene and the 3-hexene to 1-hexene;
    recovering an effluent from the isomerization reaction zone comprising 2-hexene, 3-hexene, isohexene, and 1-hexene;
    separating the isomerization effluent in a second distillation system to recover a bottoms fraction comprising 2-hexene and 3-hexene and an overheads fraction comprising 1-hexene.

2. The process of claim 1, wherein the mixed hydrocarbon stream comprises at least one of an ethylene oligomerization reaction product or a portion thereof and a $C_4$ metathesis reaction product or a portion thereof.

3. The process of claim 1, further comprising:
    separating any ether and unreacted alcohol from the first distillation system overheads fraction prior to the feeding the overheads fraction to an isomerization reaction zone to produce a stream essentially free of ethers and alcohols.

4. The process of claim 1, wherein the alcohol comprises at least one C1 to C6 primary or secondary alcohol or mixtures thereof.

5. The process of claim 1, wherein the alcohol comprises at least one of methanol, ethanol, and mixtures thereof.

6. The process of claim 1, wherein the conditions of temperature and pressure for contacting the isohexene and the alcohol with the etherification catalyst comprises a temperature is in the range from about 60° C. to about 100° C.

7. The process of claim 1, wherein the conditions of temperature and pressure for contacting the 2-hexene and 3-hexene with the isomerization catalyst comprises a:
    a temperature is in the range from about 60° C. to about 100° C.; and
    a pressure in the range from about 2 to about 40 bar.

8. The process of claim 1, further comprising recycling at least a portion of the bottoms fraction comprising 2-hexene and 3-hexene to the contacting the 2-hexene and 3-hexene with the isomerization catalyst.

9. The process of claim 1, wherein the 1-hexene and the alcohol are fed to the etherification reaction zone at a molar ratio in the range from about 1:1 to about 1:1.5, respectively.

10. The process of claim 1, wherein the etherification reaction zone comprises at least one of a fixed bed reactor, a catalytic distillation reactor system, and combinations thereof.

11. The process of claim 1, further comprising
    feeding a portion of the overheads fraction comprising unreacted alcohol and 1-hexene to a fixed bed reactor system containing a second etherification catalyst, which may be the same or different than the etherification catalyst;
    contacting the isohexene and the alcohol in the presence of the second etherification catalyst at conditions of temperature and pressure to convert at least a portion of the isohexene and the alcohol to an ether;
    recovering an effluent from the fixed bed reactor system comprising ether, 2-hexene, 3-hexene, and any unreacted alcohol and isohexene;
    feeding the effluent from the fixed bed reactor system to the separating the etherification reactor effluent.

12. A process for upgrading a mixed hexene stream, the process comprising:
feeding an alcohol and mixed hydrocarbon stream comprising isohexene, 2-hexene, and 3-hexene to an etherification reaction zone containing an etherification catalyst;
contacting the isohexene and the alcohol in the presence of the etherification catalyst at reaction conditions of temperature and pressure to convert at least a portion of the isohexene and the alcohol to an ether;
recovering an effluent from the etherification reactor comprising ether, 2-hexene, 3-hexene, and unreacted alcohol and isohexene;
separating the etherification reactor effluent in a first distillation system to recover a bottoms fraction comprising the ether and an overheads fraction comprising the 2-hexene, 3-hexene, and the unreacted alcohol and isohexene;
feeding a portion of the overheads fraction comprising unreacted alcohol and 1-hexene to a fixed bed reactor system containing a second etherification catalyst, which may be the same or different than the etherification catalyst;
contacting the isohexene and the alcohol in the presence of the second etherification catalyst at conditions of temperature and pressure to convert at least a portion of the isohexene and the alcohol to an ether;
recovering an effluent from the fixed bed reactor system comprising ether, 2-hexene, 3-hexene, and any unreacted alcohol and isohexene;
feeding the effluent from the fixed bed reactor system to the separating the etherification reactor effluent;
feeding a portion of the overheads fraction to an isomerization reaction zone containing an isomerization catalyst;
contacting the 2-hexene and 3-hexene in the overheads fraction with the isomerization catalyst at conditions of temperature and pressure to convert at least a portion of the 2-hexene and the 3-hexene to 1-hexene;
recovering an effluent from the isomerization reaction zone comprising 2-hexene, 3-hexene, isohexene, and 1-hexene;
separating the isomerization effluent in a second distillation system to recover a bottoms fraction comprising 2-hexene and 3-hexene and an overheads fraction comprising 1-hexene.

13. The process of claim 12, wherein the hydrocarbon stream comprises $C_{5-}$ hydrocarbons, the process further comprising:
fractionating a hydrocarbon stream comprising $C_{5-}$ hydrocarbons and C6 hydrocarbons including isohexene, 2-hexene, and 3-hexene to recover $C_{5-}$ hydrocarbons as an overhead fraction and C6 and any heavier hydrocarbons as the hydrocarbon stream comprising isohexene, 2-hexene, and 3-hexene.

14. The process of claim 13, wherein the hydrocarbon stream comprises at least one of an ethylene oligomerization reaction product or a portion thereof and a $C_4$ metathesis reaction product or a portion thereof.

15. The process of claim 12, further comprising:
separating any ether and unreacted alcohol from the first distillation system overheads fraction prior to the feeding the overheads fraction to the isomerization reaction zone to produce a stream essentially free of ethers and alcohols.

16. The process of claim 12, wherein the alcohol comprises at least one C1 to C6 primary or secondary alcohol or mixtures thereof.

17. The process of claim 12, wherein the alcohol comprises at least one of methanol, ethanol, and mixtures thereof.

18. The process of claim 12, wherein the conditions of temperature and pressure for contacting the isohexene and the alcohol with the etherification catalyst comprises a temperature is in the range from about 60° C. to about 100° C.

19. The process of claim 12, wherein the conditions of temperature and pressure for contacting the 2-hexene and 3-hexene with the isomerization catalyst comprises a:
a temperature is in the range from about 60° C. to about 100° C.; and
a pressure in the range from about 2 to about 40 bar.

20. The process of claim 12, wherein the second distillation system comprises a first distillation column and a second distillation column, the separating comprising:
feeding a portion of the effluent from the isomerization reaction zone to each of the first and the second distillation columns;
fractionating in the first distillation column the portion of the effluent fed to the first distillation column to recover a bottoms fraction comprising 2-hexene and 3-hexene and an overheads fraction comprising 1-hexene, 2-hexene, and 3-hexene;
feeding the first distillation column overheads fraction to the second distillation column;
fractionating in the second distillation column the portion of the effluent fed to the second distillation column and the first distillation column overheads fraction to recover a bottoms fraction comprising 2-hexene and 3-hexene and an overheads fraction comprising 1-hexene.

21. The process of claim 20, further comprising recycling at least a portion of the bottoms fractions from the first and second distillation columns to the contacting the 2-hexene and 3-hexene with the isomerization catalyst.

22. The process of claim 12, wherein the 1-hexene and the alcohol are fed to the etherification reaction zone at a molar ratio in the range from about 1:1 to about 1:1.5, respectively.

23. A process for upgrading a mixed hexene stream, the process comprising:
feeding an alcohol and a mixed hydrocarbon stream comprising isohexene, 2-hexene, and 3-hexene to an etherification reaction zone containing an etherification catalyst;
contacting the isohexene and the alcohol in the presence of the etherification catalyst at reaction conditions of temperature and pressure to convert at least a portion of the isohexene and the alcohol to an ether;
recovering an effluent from the etherification reaction zone comprising ether, 2-hexene, 3-hexene, and unreacted alcohol and isohexene;
feeding the effluent from the etherification reaction zone to a catalytic distillation reactor system containing a second etherification catalyst, which may be the same or different than the etherification catalyst;
concurrently in the catalytic distillation reactor system:
contacting the isohexene and the alcohol in the presence of the second etherification catalyst at conditions of temperature and pressure to convert at least a portion of the isohexene and the alcohol to additional ether;
separating the etherification reactor effluent and the additional ether to recover a bottoms fraction comprising the ether and an overheads fraction comprising the 2-hexene, 3-hexene, and any unreacted alcohol and isohexene;

feeding at least a portion of the overheads fraction to an isomerization reaction zone containing an isomerization catalyst;

contacting the 2-hexene and 3-hexene in the overheads fraction with the isomerization catalyst at conditions of temperature and pressure to convert at least a portion of the 2-hexene and the 3-hexene to 1-hexene;

recovering an effluent from the isomerization reaction zone comprising 2-hexene, 3-hexene, isohexene, and 1-hexene;

separating the isomerization effluent in a second distillation system to recover a bottoms fraction comprising 2-hexene and 3-hexene and an overheads fraction comprising 1-hexene.

24. The process of claim 23, wherein the hydrocarbon stream comprises $C_{5-}$ hydrocarbons, the process further comprising:

fractionating a hydrocarbon stream comprising $C_{5-}$ hydrocarbons and C6 hydrocarbons including isohexene, 2-hexene, and 3-hexene to recover $C_{5-}$ hydrocarbons as an overhead fraction and C6 and any heavier hydrocarbons as the hydrocarbon stream comprising isohexene, 2-hexene, and 3-hexene.

25. The process of claim 24, wherein the hydrocarbon stream comprises at least one of an ethylene oligomerization reaction product or a portion thereof and a $C_4$ metathesis reaction product or a portion thereof.

26. The process of claim 23, further comprising:

separating any ether and unreacted alcohol from the catalytic distillation reactor system overheads fraction prior to the feeding the overheads fraction to the isomerization reaction zone to produce a stream essentially free of ethers and alcohols.

27. The process of claim 23, wherein the alcohol comprises at least one $C_1$ to $C_6$ primary or secondary alcohol or mixtures thereof.

28. The process of claim 23, wherein the alcohol comprises at least one of methanol, ethanol, and mixtures thereof.

29. The process of claim 23, wherein the conditions of temperature and pressure for contacting the isohexene and the alcohol with the etherification catalyst comprises a temperature is in the range from about 60° C. to about 100° C.

30. The process of claim 23, wherein the conditions of temperature and pressure for contacting the 2-hexene and 3-hexene with the isomerization catalyst comprises a:

a temperature is in the range from about 60° C. to about 100° C.; and a pressure in the range from about 2 to about 40 bar.

31. The process of claim 23, wherein the second distillation system comprises a first distillation column and a second distillation column, the separating comprising:

feeding a portion of the effluent from the isomerization reaction zone to each of the first and the second distillation columns;

fractionating in the first distillation column the portion of the effluent fed to the first distillation column to recover a bottoms fraction comprising 2-hexene and 3-hexene and an overheads fraction comprising 1-hexene, 2-hexene, and 3-hexene;

feeding the first distillation column overheads fraction to the second distillation column;

fractionating in the second distillation column the portion of the effluent fed to the second distillation column and the first distillation column overheads fraction to recover a bottoms fraction comprising 2-hexene and 3-hexene and an overheads fraction comprising 1-hexene.

32. The process of claim 31, further comprising recycling at least a portion of the bottoms fractions from the first and second distillation columns to the contacting the 2-hexene and 3-hexene with the isomerization catalyst.

33. The process of claim 23, wherein the 1-hexene and the alcohol are fed to the etherification reaction zone at a molar ratio in the range from about 1:1 to about 1:1.5, respectively.

* * * * *